(12) United States Patent
Kojima et al.

(10) Patent No.: US 6,703,225 B1
(45) Date of Patent: Mar. 9, 2004

(54) INTERFERON-α

(75) Inventors: Shin-ichi Kojima, Kobe (JP); Akira Asakura, Kawanishi (JP); Tetsuaki Futatsugi, Otsu (JP); Yuko Ota, Nishinomiya (JP); Yuki Fukuda, Nishinomiya (JP); Shinsuke Sagara, Suita (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/889,035

(22) PCT Filed: Jan. 4, 2000

(86) PCT No.: PCT/JP00/00015

§ 371 (c)(1),
(2), (4) Date: Oct. 24, 2001

(87) PCT Pub. No.: WO00/42186

PCT Pub. Date: Jul. 20, 2000

(30) Foreign Application Priority Data

Jan. 12, 1999 (JP) ............................................ 11/005138

(51) Int. Cl.⁷ ..................... C12P 21/04; C07K 17/00; A61K 38/21; C07H 21/04
(52) U.S. Cl. .................. 435/69.51; 530/351; 424/85.7; 424/85.4; 536/23.52
(58) Field of Search .................... 530/351; 424/85.2, 424/85.4; 435/69.51; 536/23.52

(56) References Cited

U.S. PATENT DOCUMENTS 5,789,551 A * 8/1998 Pestka ........................ 530/351

FOREIGN PATENT DOCUMENTS

WO WO-8302457 * 7/1983

OTHER PUBLICATIONS

Goeddel et al., "The structure of eight distinct cloned human leukocyte interferon cDNAs", *Nature*, vol. 290, Mar. 5, 1981, pp. 20–26.

Lund et al., "Differential expression of Interferon genes in a substrain of Namalwa cells", *Journal of Interferon Research*, vol. 5, No. 2, 1985, pp. 229–238.

Bartholomew et al., "Identification of a functional allele of a human Interferon–α gene previously characterized as a pseudogene", *Journal of Interferon Research*, vol. 9, No. 4, Aug. 1989, pp. 407–417.

Shafferman et al., "Specific residues within an amino–terminal domain of 35 residues of interferon alpha are responsible for recognition of the human interferon alpha cell receptor and for triggering biological effects", *J. Biol. Chem.*, vol. 262, No. 13, May 5, 1987, pp. 6227–6237.

Tymms et al., "Functional significance of amino acidresidues with conserved hydrophilic regions in human interferons–α", *Antiviral Research*, vol. 12, No. 1, 1989, pp. 37–48.

Henco et al., "Structural Relationship of Human Interferon Alpha Genes and Pseudogenes", *J. Mol. Biol.*, vol. 185, 1985, pp. 227–260.

* cited by examiner

Primary Examiner—Lorraine Spector
Assistant Examiner—Janet L. Andres
(74) Attorney, Agent, or Firm—Sughrue Mion, PLLC

(57) ABSTRACT

A novel human IFN-α subtype and its derivative having an unprecedentedly high specific activity, DNA encoding these proteins, an expression vector having said DNA, a transformant transformed with said expression vector, a method of producing the above human IFN-α and its derivative, and medical uses of the above human IFN-α and its derivative.

5 Claims, No Drawings

INTERFERON-α

TECHNICAL FIELD

The present invention relates to a novel interferon-α (hereinafter referred to as IFN-α). More preferably, the present invention relates to a novel human IFN-α and its derivative having an unprecedentedly high specific activity, and a gene thereof, as well as medical uses of said IFN-α and its derivative.

BACKGROUND ART

IFN is a generic term for proteins having anti-viral activity, among which those produced from leukocytes or lymphoblastic cells by stimulation with virus or double stranded nucleic acids are termed as IFN-α. IFN-α has a variety of activities including anti-viral activity and a cellular growth-suppressing activity, which activities have been found to be useful in a variety of diseases such as hepatitis type B, hepatitis type C, and cancer.

Analysis of base sequences of IFN-α genes cloned from a variety of DNA libraries have revealed that IFN-α has several subtypes (Science 209: 1343–7 (1980), Gene 11: 181–6 (1980), Nature 290: 20–26 (1981), Nature 313: 698–700 (1985), J. Invest. Dermatol. 83: 128s–136s (1984)). For example, for the main subtype gene of IFN-α2, three types(α2a, α2b, and α2c) have been identified (J. Interferon Res. 2: 575–85 (1982), J. Interferon Res. 13: 227–31 (1993), J. Biol. Chem. 268: 12565–9 (1993), Acta Virol. 38: 101–4 (1994), Biochim. Biophys. Acta. 1264: 363–8 (1995)). In addition, there are currently known nearly 20 types of subtype genes including IFN-α1a, -α1b, -α4a, -α4b, -α5, -α6, etc.

On the other hand, vigorous efforts have been made in structural analysis of proteins in stead of genes, that is to purify each subtype of natural IFN-α and then to analyze its primary structure. A group in Wellcome, for example, made an attempt on structural analysis using a mixture of two fractions separated by gel filtration of purified IFN derived from Namalwa cells, human lymphoblastic cells, and, as a result, have demonstrated the structure, though not complete, of IFN-α1 and IFN-α2 (Nature 287: 408–11 (1980)). As a result of intensive efforts to purify Namalwa cell-derived IFN subtypes, Zoon et al. of FDA have successfully isolated several subtypes and revealed their partial structure, anti-viral activity, cellular growth-suppressing activity, and NK cell-inducing activity (Infect. Immun. 34: 1068–70 (1981), J. Biol. Chem. 267: 15210–6 (1992), J. Biol. Chem. 268: 12591–5 (1993)). Furthermore, in the analysis of the primary structure for one major subtype, they have demonstrated that it was IFN-α2b (J. Biol. Chem. 267: 15210–6 (1992)).

As stated above, IFN-α has various subtypes, of which base sequences and amino acid sequences are being elucidated, though the structure and physical properties of all subtypes have not been revealed.

DISCLOSURE OF THE INVENTION

The present invention intends to provide a novel IFN-α and its gene. Thus, the present invention intends to provide a novel human IFN-α, its derivative having an unprecedentedly high specific activity, a gene encoding them, and a pharmaceutical agent comprising said IFN-α and its derivative as active ingredient.

The inventors of the present invention have attempted to isolate major subtypes contained in IFN-α derived from human natural-type lymphoblastic cells (hereinafter referred to as HLBI). Thus, the inventors have found that the subtypes can be easily separated by means of a reverse-phase HPLC that utilizes μBondasphere column and Vydac™-C4 column and thereby have successfully isolated and purified 12 major subtypes contained in HLBI.

From the analysis of the N-terminal amino acid sequence and the primary structure of the isolated subtypes, it was found that a novel IFN-α subtype was contained in addition to the existing IFN-α1, α2b, α5, α7, α8, α14, α17 and α21. The inventors of the present invention have termed this novel IFN-α subtype as IIIe.

On these subtypes, anti-viral activity against Sindbis virus was determined using human-derived cultured cells, FL cells, and it was found that the anti-viral activity of a major subtype IFN-α2b was $1.67 \times 10^8$ u/mg whereas the novel IFN-α subtype IIIe had the highest and unprecedentedly high specific activity of $4.3-5.2 \times 10^8$ u/mg.

Furthermore, the identification of the entire amino acid sequence of the subtype IIIe revealed that the primary structure of the subtype IIIe was similar to an amino acid sequence deduced from the sequence of IFN-α10a (=-αC) gene as reported in Nature Mar. 5, 1981; 290, 20–26, but had a novel amino acid sequence in which the amino acid at position 19 was Ala in stead of Gly. The cloning of said IIIe gene also revealed that it is different from IFN-α10a by three bases on the base sequence level.

As described above, the IFN-α subtype IIIe of the present invention has an unprecedentedly high specific activity, and thereby its dosage can possibly be reduced compared to commercially available recombinant human IFN-α2a, recombinant human IFN-α2b, etc. Furthermore, it is expected to exhibit effectiveness on cases with HCV-Genotype II, high virus level etc. on which conventional IFN is believed to be not very effective.

The present invention was completed based on the above findings.

Thus, the present invention relates to the following (1) to (13):

(1) DNA comprising the base sequence as set forth in SEQ ID NO: 1 or SEQ ID NO: 2, or DNA encoding a protein comprising the amino acid sequence as set forth in SEQ ID NO: 3 or SEQ ID NO: 4;

(2) DNA encoding a derivative of human interferon-α, said DNA being selected from
  (A) DNA hybridizing to the DNA according to the above (1) under a stringent condition, and
  (B) DNA encoding a protein in which one or a plurality of amino acid residues of a protein encoded by the DNA according to the above (1) have been replaced, deleted, and/or added,
  wherein the protein encoded by said DNA has the following characteristics (a) and (b):
    (a) having a specific activity higher than $4.0 \times 10^8$ units/mg as measured by an anti-viral activity assay on Sindbis virus using the FL cell, a human-derived cultured cell; and
    (b) migrating as a band with an apparent molecular weight of 20 kDa–23 kDa on a sodium dodecyl sulfate-polyacrylamide gel electrophoresis after reduction treatment;

(3) The DNA according to the above (2) which encodes a protein comprising an amino acid sequence in which 1–5 amino acid residues in the amino acid sequence as set forth in SEQ ID NO: 3 or SEQ ID NO: 4 have been replaced, deleted, and/or added;

(4) An expression vector having the DNA according to any one of the above (1)–(3);

(5) A transformant transformed with the expression vector according to the above (4);

(6) A method of producing a recombinant human interferon-α or its derivative, which method comprises culturing the transformant according to the above (5) and recovering the expressed recombinant human interferon-α or its derivative;

(7) A human interferon-α or its derivative which is encoded by the DNA according to any one of the above (1)–(3) or produced by the production method according to the above (6);

(8) A human interferon-α comprising the amino acid sequence as set forth in SEQ ID NO: 3 or SEQ ID NO: 4;

(9) A human interferon-α or its derivative according to the above (7) or (8) or a pharmaceutically acceptable salt thereof for use as active ingredient of a pharmaceutical composition;

(10) A pharmaceutical composition comprising the human interferon-α or its derivative according to the above (7) or (8) or a pharmaceutically acceptable salt thereof as active ingredient together with a pharmaceutically acceptable carrier or excipient;

(11) The pharmaceutical composition according to the above (10) which is for treatment of viral diseases;

(12) The pharmaceutical composition according to the above (10) which is for treatment of cancer;

(13) A method of treating viral diseases or cancer which method comprises administering to a mammal including a human an effective amount of the human interferon-α or its derivative according to the above (7) or (8) or a pharmaceutically acceptable salt thereof.

BEST MODE FOR CARRYING OUT THE INVENTION

The DNA of the present invention encodes a novel human IFN-α and its derivative, and specifically there can be mentioned DNA comprising the base sequence as set forth in SEQ ID NO: 1 or SEQ ID NO: 2, or DNA encoding a protein comprising the amino acid sequence as set forth in SEQ ID NO: 3 or SEQ ID NO: 4.

Also encompassed in the scope of the present invention is DNA that hybridizes to the DNA described above under a stringent condition, or DNA encoding a derivative of a human interferon-α selected from DNA encoding a protein in which one or a plurality of amino acid residues of the protein encoded by the above DNA have been replaced, deleted, and/or added, wherein the protein encoded by said DNA has the characteristics of (a) having a specific activity higher than $4.0 \times 10^8$ units/mg as measured by an anti-viral activity assay on Sindbis virus using the FL cell, a human-derived cultured cell, and (b) migrating as a band with an apparent molecular weight of 20 kDa–23 kDa on a sodium dodecyl sulfate-polyacrylamide gel electrophoresis after reduction treatment. The DNA of the present invention will now be sequentially explained below.

1) DNA Encoding the IFN-α Subtype IIIe

Among the above DNA, "DNA comprising the base sequence as set forth in SEQ ID NO: 1 or SEQ ID NO: 2" and "DNA encoding a protein comprising the amino acid sequence as set forth in SEQ ID NO: 3 or SEQ ID NO: 4" are DNA encoding the human-derived IFN-α subtype IIIe of the present invention. Among them, the base sequence as set forth in SEQ ID NO: 1 and the amino acid sequence as set forth in SEQ ID NO: 3 are a base sequence and an amino acid sequence corresponding to the full-length subtype IIIe including the signal peptide, and the base sequence as set forth in SEQ ID NO: 2 and the amino acid sequence as set forth in SEQ ID NO: 4 are a base sequence and an amino acid sequence corresponding to the full-length mature type subtype IIIe including no signal peptide.

Said DNA can be cloned by the PCR method described in Example 3 below. As templates for performing PCR, genomic DNA or cDNA derived, for example, from the Namalwa cell (ATCC™ No. CRL-1432 etc.) may be used, and as primers, a primer comprising the base sequence, for example, as set forth in SEQ ID NO: 6 and SEQ ID NO: 7 may be mentioned.

Furthermore, cloning may also be performed by modifying amino acids based on the known IFN-α subtypes reported in Nature 290: 20–26 (1981), etc. Said cloning may be readily performed by a person skilled in the art according to Molecular Cloning 2nd Ed., Cold Spring Harbor Laboratory Press (1989) etc.

2) DNA Encoding a Derivative of IFN-α Subtype IIIe

Among the above DNA, "DNA that hybridizes to the DNA of the subtype IIIe under a stringent condition" and "DNA encoding a protein in which one or a plurality of amino acid residues of the amino acid sequence of the subtype IIIe have been replaced, deleted, and/or added" mean DNA encoding a protein having a structure similar to the subtype IIIe such as an artificially constructed, so-called modified protein, an allele mutant present in the living body, and an IFN-α subtype similar to IIIe. Hereinbelow, protein having such a structure similar to the subtype IIIe will be termed as a "derivative."

As used herein, as a method of producing "DNA encoding protein in which one or a plurality of amino acid residues of the amino acid sequence of the subtype IIIe have been replaced, deleted, and/or added," there can be known methods such as site-directed mutagenesis and the PCR method, which may be easily performed by a person skilled in the art according to Nucleic Acid Res. 10: 6487 (1982), Methods in Enzymology 100: 448 (1983), Molecular Cloning 2nd Ed., Cold Spring Harbor Laboratory Press (1989), PCR A Practical Approach, IRL Press, pp. 200 (1991), etc.

As the number of amino acid residues to be modified, there can be mentioned those numbers that may be replaced, deleted, and/or added by known methods such as the site-directed mutagenesis mentioned above. Since IFN-α is a relatively small protein of which mature type comprises 166 amino acids, the number of amino acid residues to be modified is preferably 10 or less, and more preferably 5 or less. For sites that are important for activity expression, modification is preferably substitution to conservative amino acids.

As used herein, as a method of producing "DNA that hybridizes to the DNA of the subtype IIIe under a stringent condition," there can be mentioned known methods such as a PCR method, and a hybridization method. Specifically, it may be performed according to the method described in the above Molecular Cloning.

As used herein, "under a stringent condition" means a condition in which hybridization is performed at 42° C. in a solution containing 6×SSC (20×SSC represents 333 mM sodium citrate and 333 mM NaCl), 0.5% SDS, and 50% formamide, followed by washing at 68° C. in a solution of 0.1×SSC and 0.5% SDS, a condition as described in the above-mentioned Molecular Cloning, or the like. More preferably, there can be mentioned a condition in which hybridization occurs only for those that are different from the DNA of the subtype IIIe by about 1–5 amino acids.

Among the above DNA, the DNA encoding a protein which has the following characteristics can be the DNA of the present invention:(a) having a specific activity higher than $4.0 \times 10^8$ units/mg as measured by an anti-viral activity assay on Sindbis virus using human-derived cultured cells, FL cells; and (b) migrating as a band with an apparent molecular weight of 20 kDa–23 kDa on a sodium dodecyl sulfate-polyacrylamide gel electrophoresis after reduction treatment.

Whether the protein encoded by the candidate DNA that can be the DNA of the present invention satisfies the above requirement (a) can be evaluated by performing an anti-viral activity assay as described below.

Thus, 45,000–60,000 FL cells (The National Institute of Health, ATCC™ etc.) prepared in a 10 v/v % bovine calf serum-Eagle's minimum essential medium are inoculated into each well of a microtiter plate, which is incubated in a 5% carbon dioxide incubator at 37° C. for 20 hours. Then 100 µl of the candidate IFN sample is added to each well and incubated at 37° C. for 6 hours. The culture liquid is discarded and $10^5$–$10^6$ PFU of Sindbis virus (The National Institute of Health, ATTC etc.) per well is added, and incubated at 37° C. for 2 days. The cells are stained in a 0.02 w/v % Neutral red-5 v/v % bovine calf serum-Eagle's minimum essential medium, and the degree of cytopathic effect is determined by the amount of the dye incorporated.

As methods of calculating titer, the following method may be mentioned. Thus, the dye incorporated into the cell is eluted with an acidified 30 v/v % ethanol and absorbance is determined at a wavelength of 545 mµ. The experimental titer of the sample and the standard (The National Institute of Health) are calculated from the dilution factor of the sample exhibiting 50% of the absorbance of the dye incorporated into the normal cell and that of the standard. The titer of the standards and the experimental titer are used to determine a correction factor, which is used to correct the experimental titers of the samples to obtain the titers of the samples. In the above activity assay, those having a specific activity higher than $4.0 \times 10^8$ units/mg are included in the scope of the present invention.

Whether the protein encoded by the candidate DNA satisfies the above requirement (b) can be detected by subjecting the candidate protein to reduction treatment with 2-mercaptoethanol followed by a normal sodium dodecyl sulfate-polyacrylamide gel electrophoresis (SDS-PAGE) and then staining with Coomassie brilliant blue. The density of the SDS-PAGE gel at this time is preferably about 3.5% for the concentration gel and about 15% for the separation gel. Electrophoresis is preferably performed at about 50 mA. In the SDS-PAGE as described above, those having an apparent molecular weight of 20 kDA–23 kDa are included in the scope of the present invention.

By recombinant DNA technology using the DNA of the present invention, the protein of the present invention, that is, the novel human IFN-α subtype IIIe and its derivative can be produced in large quantities. In order to produce the recombinant human IFN-α and its derivative of the present invention by expressing the DNA of the present invention, methods are used, for example, based on many textbooks and references including the above Molecular Cloning. For human IFN-α2a and -α2b, their recombinant types have already been produced and are commercially available. Based on the production method for known IFN-α, the novel human IFN-α and its derivative of the present invention can be produced in large quantities (see Japanese Examined Patent Publication (Kokoku) No. 63-63198, Japanese Examined Patent Publication (Kokoku) No. 3-21151, Nucleic Acids Res. 8: 4057 (1981), Nature 287: 411 (1980), Proc. Natl. Acad. Sci. USA 77: 5230 (1980), and the like).

Specifically, by optionally adding a regulatory gene such as a promoter sequence (for example, trp, lac, T7, and SV40 early promoter) that controls transcription to the upstream of the DNA to be expressed, which is then integrated into a suitable vector (for example, PBK-CMV, pCAGGS, and pZeoSV), it is possible to construct an expression vector that is replicated and expressed in the host cell. Then said expression vector is introduced into a suitable host cell to obtain a transformant. As the host cell, there can be mentioned a prokaryote such as Escherichia coli, a unicellular eukaryote such as yeast, a multicellular eukaryote such as an insect or an animal, and the like. As the method of introducing an expression vector into a host cell, a known method can be used such as the calcium phosphate method, the DEAE-dextran method, and the electric pulse method. By culturing the thus obtained transformant in a culture medium suitable for said transformant by a standard method, the desired recombinant human IFN-α and its derivative of the present invention can be produced. The recombinant human IFN-α and its derivative of the present invention obtained in this manner can be isolated and purified by a common biochemical method using, for example, anti-IFN-α antibody.

Furthermore, they can also be obtained by purifying a subtype obtained by using as raw material the human natural type lymphoblast-derived IFN-α (HLBI) (manufactured by Sumitomo Pharmaceutical Co., Ltd.) as described in Example 1 below.

The novel human IFN-α subtype IIIe and its derivative of the present invention thus obtained are encoded by the above DNA of the present invention, and they are proteins produced by the expression of the latter. As a specific example, there may be illustrated the novel human IFN-α subtype IIIe of the present invention comprising the amino acid sequence as set forth in SEQ ID NO: 3 or SEQ ID NO: 4.

The novel IFN-α and its derivative of the present invention can be used as active ingredient of pharmaceutical agents. Thus the present invention also intends to provide a pharmaceutical composition comprising a novel IFN-α and its derivative or a pharmaceutically acceptable salt thereof together with a pharmaceutically acceptable carrier or excipient, and optionally with another therapeutic and/or preventive agent.

It is conventionally known that IFN-α has a variety of effects including an anti-viral effect, a cellular growth-suppressing effect, a natural killer cell-activating effect, and the like. Accordingly, the novel IFN-α of the present invention is also expected to be able to treat various diseases based on these effects.

As the indicated diseases, cancer (malignant tumor), viral diseases, and immunological diseases may be mentioned, and specifically there can be mentioned kidney cancer, renal-cell carcinoma, breast cancer, bladder cancer, basal cell carcinoma, head and neck cancer, cervical dysplasia, skin carcinoma, Kaposi's sarcoma, malignant melanoma, non-Hodgkin lymphoma, infant hemangioma, chronic granulomatosis, type B chronic hepatitis, type C chronic hepatitis (active, non-active), herpes infections (genital herpes, corneal herpes inflammation, oral herpes inflammation, etc.), chronic myelocytic leukemia (CML), adult T cell leukemia, hairy cell leukemia, hairy cell leukemia, T cell leukemia virus (HTLV-1) myelopathy, multiple myeloma, lymphoma, subacute sclerosing panencephalitis (SSPE), Sjogren's syndrome, condyloma acuminata, AIDS, multiple sclerosis (MS), stomatitis, genital wart, intravaginal wart, erythrocytosis, thrombocythemia, psoriasis, mycosis fungoides, sudden deafness, senile disciform macular degeneration, Paget's disease, and the like.

Since the IFN-α and its derivative of the present invention has a specific activity higher than the conventional ones, they are expected to be effective on cases with HCV-Genotype II, high virus level etc. on which conventional IFN is said to be not very effective.

The novel interferon-α and its derivative of the present invention or a pharmaceutically acceptable salt thereof may be administered as a pharmaceutical composition via an oral or parenteral (for example, intravenous, subcutaneous or intramuscular injection, local, transrectal, transdermal, or nasal) route. As compositions for oral administration, there can be mentioned, for example, tablets, capsules, pills, granules, powders, liquids, and suspensions, and as compositions for parenteral administration, there can be mentioned, for example, aqueous or oily agents for injection, ointments, creams, lotions, aerosols, suppositories, and adhesives. It is also possible to prepare sustained release minipellet formulations and implant them near the affected area, or to gradually administer them to the affected area on a continuous basis using an osmotic pump. These formulations may be prepared using conventionally known technology, and may contain non-toxic and inert carriers or excipients that are commonly used in the field of pharmaceutics.

The above pharmaceutical compositions may be manufactured by blending the active ingredient of the present invention with pharmaceutically acceptable conventional carriers, excipients, binders, stabilizers, buffers, solution adjuvants, or tonicity agents. When used as injections, there may be added buffers, solution adjuvants, tonicity agents etc.

The dosage and the frequency of administration may vary depending on the condition and history of the disease, age and weight of the patient, dosage form, etc., but when they are administered to adults (body weight 60 kg) via a parenteral (for example, intravenous) route, they are generally prepared, as appropriate, in the range of 0.001–1 mg per day, preferably 0.005–0.5 mg, and most preferably 0.010–0.2 mg, and administered in single or several divided doses.

The present invention will now be explained in further details hereinbelow with reference to examples, but it should noted that the present invention will not be limited by these examples in any way.

EXAMPLE 1

Isolation of each IFN-α Subtype, and the Measurement of its Physical Properties and Biological Activity In order to elucidate the physical properties and partial structures in detail of major natural-type IFN-α subtypes contained in HLBI, IFN-α subtypes were isolated. It was found that each subtype can be isolated by a reverse phase HPLC method using the μBondasphere (5μ, C4, 300A) column manufactured by Water's and the RP-304 column (Vydac™-C4 column) manufactured by Bio-Rad™ that have slightly different subtype-separation characteristics from each other, and therefore the present method was routinely used.

After extensive study, 12 IFN-α subtypes each being different from one another were isolated and then each IFN-α subtype was subjected to purity analysis using the reductive SDS-PAGE method. Furthermore, each IFN-α subtype was subjected to amino acid analysis, molecular weight determination by the reductive SDS-PAGE method, and the amino acid sequencing of the amino terminal to clarify its physical properties. In addition, in order to elucidate the biological activity, the FL (amniotic) cell, a human-derived cultured cell, was used as a test cell and its anti-viral activity on Sindbis virus was determined. The experimental method and result are described below.

Experimental Method

1) IFN-α Samples

A total of two lots, a subpool lot No. PS/199 (50 ml) and a subpool lot No. PS/200 (50 ml) that are intermediate products of HLBI were used as the samples for isolation of IFN-α subtypes.

2) Fractionation of IFN-α Sample (Lot No. PS/199)

After thawing, the sample was centrifuged at a high speed of 12,000 rpm at 4° C. for 10 minutes, and 45 ml of the supernatant obtained was used. After passing 45 ml of the supernatant at a flow rate of 3 ml/min through the Water's μBondasphere (5μ, C4, 300A) column (19φ×150 mm) pre-equilibrated with a 0.1% TFA solution, 15 ml of the 0.1% TFA solution was run at a flow rate of 3 ml/min, and then the column was extensively washed by passing 24 ml of the 0.1% TFA solution at a flow rate of 8 ml/min. Then by a gradient method in which acetonitrile concentration was increased, IFN-α subtypes were eluted.

The eluate was monitored at A280 nm to fractionate at 4 ml/Fr. RP-HPLC was performed under the following condition.

RP-HPLC Condition

High performance liquid chromatography instrument: LC6A manufactured by Shimadzu™

Column: Water's μBondasphere (5μ, C4, 300A) column (190φ×150 mm)

Flow rate: 8 ml/min

Eluent A: 0.1% TFA, eluent B: 0.1% TFA-95% acetonitrile

Gradient elution condition: As described in Table 1

TABLE 1

| Time: min | 0 | 3 | 35 | 75 | 95 | 105 | 115 | 115.1 |
|---|---|---|---|---|---|---|---|---|
| Solution B % | 0 | 30 | 46 | 52 | 55 | 60 | 100 | 0 |

Detection: A280 nm, 0.04 aufs

Fractionation: 4 ml/Fr

3) Fractionation of the IFN-α Sample (Lot No. PS/200)

After thawing, the sample was centrifuged at a high speed of 12,000 rpm at 4° C. for 10 minutes, and 45 ml of the supernatant obtained was used. After passing 45 ml of the supernatant at a flow rate of 3 ml/min through the Water's μBondasphere (5μ, C4, 300A) column (19φ×150 mm) pre-equilibrated with a 0.1% TFA solution, 15 ml of the 0.1% TFA solution was run at a flow rate of 3 ml/min, and then the column was extensively washed by passing 24 ml of the 0.1% TFA solution at a flow rate of 8 ml/min. Then by a gradient method in which acetonitrile concentration was increased, IFN-α subtypes were eluted.

The eluate was monitored at A280 nm to fractionate at 4 ml/Fr. RP-HPLC was performed under the above condition 2).

4) Isolation of IFN-α Subtypes

Fractions obtained in the above 2) and 3) were subjected to purification by the reverse phase HPLC method using the RP-304 column manufactured by Bio-Rad™. An equal amount of a 0.1% TFA solution was added to each fraction, and then equilibrated with the 0.1% TFA solution. After running at a flow rate of 1 ml/min through the Bio-Rad™'s RP-304 (5μ, C4, 300A) column (4.6φ×250 mm), the column was extensively washed by passing 15 ml of the 0.1% TFA solution at a flow rate of 1 ml/min. Then by a gradient method in which acetonitrile concentration was increased, IFN-α subtypes were eluted. The eluate was monitored at A220 nm to fractionate at 0.3 or 0.4 ml/Fr. RP-HPLC was performed for each fraction under the following condition. Furthermore, each IFN-α subtype was chromatographed until a single peak was obtained on RP-HPLC.

RP-HPLC Condition

High performance liquid chromatography instrument: 5000 LC manufactured by Varian™

Column: RP-304 (5μ, C4, 300A) column (4.6φ×250 mm) manufactured by Bio-Rad™

Flow rate: 1 ml/min

Eluent A: 0.1% TFA, eluent B: 0.1% TFA-95% acetonitrile

Gradient elution condition: As described in Table 2

TABLE 2

| Time: min | 0 | 3 | 5 | 45 | 65 |
|---|---|---|---|---|---|
| Solution B % | 0 | 40 | 46 | 50 | 52 |

Detection: A220 nm, 0.64–2.56 aufs

Fractionation: 0.3 or 0.4 ml/Fr

5) Purity Analysis by the Reverse Phase HPLC of IFN-α Subtypes

The above isolated IFN-α subtypes were subjected to purity analysis by a reverse phase HPLC method using the Bio-Rad™'s RP-304 (5μ, C4, 300A) column.

RP-HPLC Condition

High performance liquid chromatography instrument: LC4A manufactured by Shimadzu™

Column: RP-304 manufactured by Bio-Rad™ (5μ, C4, 300A) column (4.6φ×250 mm)

Flow rate: 1 ml/min

Eluent A: 0.1% TFA-40% acetonitrile, eluent B: 0.1% TFA-50% acetonitrile

Gradient elution condition: As described in Table 3

TABLE 3

| Time: min | 0 | 2 | 42 | 42.1 |
|---|---|---|---|---|
| Solution B % | 0 | 20 | 100 | 0 |

Detection: A220 nm

6) Purity Analysis by the SDS-PAGE Method of the IFN-α Subtype

The above isolated IFN-α subtypes were subjected to purity analysis by the SDS-PAGE method. After about 0.1–0.3 μg of each IFN-α subtype was concentrated without heating by a speedvac concentrator under reduced pressure, 2-mercaptoethanol was added and then reduced at 100° C. for 1.5 minutes. An electrophoresis gel having a concentrating gel concentration of 3.5% and a separating gel concentration of 15% was used. After preelectrophoresis at 40 mA, SDS-PAGE analysis was performed by electrophoresing at 50 mA. After the electrophoresis, it was stained with a CBB solution.

7) Analysis of the Amino Acid Composition of IFN-α Subtypes

To 20–100 μl of the IFN-α subtype solutions isolated above, 1 nmol of Nle was added as an internal standard, and concentrated by a speedvac concentrator under reduced pressure. 0.2 ml of constant boiling hydrochloric acid containing 0.1% thioglycolic acid was added, and then sealed under reduced pressure and hydrolyzed at 110° C. for 24 hours. Using the automatic amino acid analyzer model 835 manufactured by Hitachi Seisakusho, the constituent amino acids that formed were analyzed by the OPA hypo method, and amino sugars and Trp were analyzed by the OPA method. Based on the analytical result of amino acid composition, the protein concentration of each IFN-α subtype was calculated.

8) Amino Terminal-amino Acid Sequencing of IFN-α Subtypes

The above isolated IFN-α subtypes were subjected to automatic Edman degradation using the gas-phase type protein sequencer model 477A manufactured by Applied Biosystems™, and the PTH-amino acids that formed were identified using the PTH-amino acid analyzer model 120A manufactured by Applied Biosystems™.

9) Anti-viral Activity of IFN-α Subtypes

As the test cell for anti-viral activity, the FL (amniotic) cell, a human-derived cultured cell, was used. The cell was provided by the National Institute of Health. The medium used was a MEM medium containing 10% fetal calf serum. Cell culture was performed at 37° C. under 5% CO2. The virus used was Sindbis virus (SBV) provided from the National Institute of Health. SBV was used to prepared a virus stock using developing chicken eggs. As the standard IFN for anti-viral activity determination, the national standard Lot. J-501 (obtained from the National Institute of Health) was used. Specific activity was expressed per mg of protein with the concentration that inhibits 50% of the virus being defined as one unit. The detailed method of measurement is shown below.

First, 45,000–60,000 FL cells prepared in a 10 v/v % bovine calf serum-Eagle's minimum essential medium were inoculated into each well of a microtiter plate, which was incubated in a 5% carbon dioxide incubator at 37° C. for 20 hours. Then 100 μl of each IFN sample was added to each well and incubated at 37° C. for 6 hours. The culture liquid was discarded and $10^5$–$10^6$ PFU of Sindbis virus per well was added, and incubated at 37° C. for 2 days. The cells were stained in a 0.02 w/v % Neutral red –5 v/v % bovine calf serum-Eagle's minimum essential medium, and the degree of cytopathic effect was determined by the amount of the dye incorporated.

Titer was calculated as follows. Thus, the dye incorporated into the cell was eluted with an acidified 30 v/v % ethanol and absorbance was determined at a wavelength of 545 mμ. The experimental titer of the sample and the standard were calculated from the dilution factor of the sample exhibiting 50% of the absorbance of the dye incorporated into the normal cell and that of the standard. The titer of the standard and its experimental titer were used to determine a correction factor, which was used to correct the experimental titers of the sample to obtain the titers of the samples.

Experimental Results and Discussion

1) Isolation of IFN-α Subtypes

According to the above experimental methods 2) and 3), the supernatant of the subpool lot No. PS/199 (45 ml) and the supernatant of the subpool lot No. PS/200 (45 ml) were fractionated by the Water's μBondasphere (5μ, C4, 300A)

column (19φ×150 mm). There were ten major fractions: fr.4, fr.8, fr.9, fr.11, fr.14, fr.18, fr.19, fr.21, fr.24, and fr.25.

Then, according to the above experimental method 4), RP-HPLC RP-HPLC preparation was performed for each fraction using the Bio-Rad™'s RP-304 (5μ, C4, 300A) column to obtain 12 IFN-α subtype fractions. As a result of purity analysis performed in accordance with the method in 5) above for each fraction by the reverse phase HPLC method using the RP-304 (5μ, C4, 300A) column, every sample exhibited a single peak confirming a high purity.

Furthermore, according to the above experimental method 6), purity analysis by the SDS-PAGE method was performed for each fraction after reduction treatment, and every sample exhibited a single band confirming the high purity. The molecular weight obtained by the SDS-PAGE method is shown in Table 4 below.

TABLE 4

| IFN-α subtype fr. No. | Molecular weight kDa |
| --- | --- |
| 4 | 26.8 |
| 8A | 22.3 |
| 9 | 21.6 |
| 11A | 22.6 |
| 11B | 20.9 |
| 14 | 22.4 |
| 18A | 21.2 |
| 18'B | 22.2 |
| 19B1 | 20.9 |
| 21 | 28.2 |
| 24 | 23.0 |
| 25 | 22.6 |

2) Amino Terminal-amino Acid Sequence Analysis of IFN-α Subtypes

For 12 IFN-α subtypes isolated, the amino acid sequence of the amino terminal was analyzed according to the above experimental method 8) to obtain the following result.

The amino terminal-amino acid sequence of IFN-α subtypes fr.8A and fr.9 coincided with the previously published sequence of IFN-α2b.

The amino terminal-amino acid sequence of IFN-α subtype fr.4 coincided with the previously published sequence of IFN-α14.

The amino terminal-amino acid sequence of IFN-α subtype fr.11A coincided with the previously published sequence of IFN-α21.

The amino terminal-amino acid sequence of IFN-α subtype fr.11B coincided with the previously published sequence of IFN-α5.

The amino terminal-amino acid sequence of IFN-α subtype fr.18A coincided with the previously published sequence of IFN-α17.

The amino terminal-amino acid sequence of IFN-α subtype fr.18'B coincided with the previously published sequence of IFN-α7.

The amino terminal-amino acid sequence of IFN-α subtype fr.19B1 coincided with the previously published sequence of IFN-α17.

The amino terminal-amino acid sequence of IFN-α subtype fr.21 coincided with the previously published sequence of IFN-α8.

The amino terminal-amino acid sequence of IFN-α subtypes fr.24 and fr.25 coincided with the previously published sequence of IFN-α1.

The amino terminal-amino acid sequence of IFN-α subtype fr.14 was similar to that of the previously published IFN-α10a (=-αC) (Nature 1981 March 5: 290, 20–26), except that the sequence was novel in that the amino acid at position 19 was Ala in stead of Gly. We have termed this novel subtype IIIe. The amino terminal-amino acid sequence of the subtype IIIe is shown in SEQ ID NO: 5.

3) Anti-viral Activity of IFN-α Subtypes

According to the above experimental method 9), anti-viral activity on Sindbis virus (SBV) was determined. The anti-viral activity of each IFN subtype is shown in Table 5 below.

All IFN subtypes showed anti-viral activity and the anti-viral activity of fr.8A (IFN-α2b), a major IFN subtype of HLBI, was $1.67 \times 10^8$ u/mg. The IFN-α subtype that had the highest specific activity was fr.14 (IIIe), and its anti-viral activity was $5.21 \times 10^8$ u/mg which is higher than that of any other conventionally known IFN-α subtypes. On the other hand, the IFN-α subtype that had the lowest specific activity was fr.24, and its anti-viral activity was $0.12 \times 10^8$ u/mg. Thus, it was demonstrated that the novel IFN subtype fr.14 (IIIe) had the highest anti-viral activity and IFN subtype fr.24 whose amino terminal-amino acid sequence coincides with that of IFN-α1 had the lowest anti-viral activity.

TABLE 5

| IFN-α subtype fr. No | Classification based on the amino terminal-amino acid sequence | Activity $\times 10^8$ u/mg |
| --- | --- | --- |
| 4 | IFN-α14 | 1.73 |
| 8A | IFN-α2b | 1.67 |
| 9 | IFN-α2b | 1.83 |
| 11A | IFN-α21 | 1.69 |
| 11B | IFN-α5 | 1.44 |
| 14 (IIIe) |  | 5.21 |
| 18A | IFN-α17 | 2.63 |
| 18'B | IFN-α7 | 1.65 |
| 19B1 | IFN-α17 | 2.57 |
| 21 | IFN-α8 | 1.50 |
| 24 | IFN-α1 | 0.12 |
| 25 | IFN-α1 | 0.20 |

EXAMPLE 2

Analysis of the Primary Structure of the IFN-α Subtype IIIe

The IFN-α subtype IIIe obtained in Example 1 is a subtype that has a novel amino acid sequence and exhibits an unprecedentedly high specific activity. In order to determine the primary structure of said IIIe, the following experiment was performed.

Experimental Method

1) Analysis of Primary Structure of the IFN-α Subtype IIIe

As the method of analyzing primary structure, a method of cleaving the Met residue with cyanogen bromide and a method of cleaving the basic amino acid residue with trypsin were employed.

The method of Cleaving a Met Residue with Cyanogen Bromide

30 μg of the IFN-α subtype IIIe was dissolved in 200 μl of 70% formic acid, to which 1 μmole of cyanogen bromide was added and allowed to stand at 24° C. for 20 hours. After the disappearance of the raw material IIIe was confirmed by a reverse phase HPLC using the PR-304 column, 9 volumes of water was added to stop the reaction and then concentrated under reduced pressure by a speedvac concentrator equipped with a NaOH trap.

To the cyanogen bromide-fragmented peptides, 0.2 ml of a 0.5 M Tris solution (pH 8.1) containing argon gas-displaced 6M guanidine and 2 mM EDTA was added and dissolved. After adding 0.4 μmole of DTT and displaced with argon gas, it was placed in the dark and was reduced at 37° C. for 3 hours. 0.8 μmole of monoiodo acetamide that was recrystalized was added, and alkylated in the dark at 37° C. for 1 hour. After passing the reaction solution at a flow rate of 1 ml/min through the RP-304 (5μ, C4, 300A) column (4.6φ×250 mm) manufactured by Bio-Rad™ previously equilibrated with a 0.1% TFA solution, the column was extensively washed by passing 15 ml of the 0.1% TFA solution at a flow rate of 1 ml/min. Then, by a gradient method in which acetonitrile concentration was increased, the constituent peptides were eluted. The eluate was monitored at A220 nm. It was purified under the following RP-HPLC condition.

RP-HPLC Condition

High performance liquid chromatography instrument: 5000 LC manufactured by Varian™

Column: RP-304 (5μ, C4, 300A) column (4.6φ×250 mm) manufactured by Bio-Rad™

Flow rate: 1 ml/min

Eluent A: 0.1% TFA, eluent B: 0.1% TFA-95% acetonitrile

Gradient elution condition: As described in Table 6

TABLE 6

| Time: min | 0 | 60 | 70 |
|---|---|---|---|
| Solution B % | 0 | 60 | 100 |

Detection: A220 nm, 1.28 aufs and A280 nm, 0.16 aufs

2) The method of Cleaving with Trypsin and the Reductive Carboxymethylation Method 60 μg of the subtype IIIe was dissolved in 200 μl of a 0.2 M NaHCO₃ (pH 8.3) solution, to which 2 μg Of TPCK-Trypsin was added and the mixture was allowed to stand at 37° C. for 24 hours. To the trypsin-fragmented peptides, 0.05 ml of a 0.5 M Tris solution (pH 8.1) containing argon gas-displaced 6M guanidine and 2 mM EDTA was added and dissolved. After adding DTT at an amount of 50 times that of the Cys residue and displaced with argon gas, it was placed in the dark and was reduced at 37° C. for 1 hour. Monoiodo acetamide that was recrystalized was added at an amount of 100 times that of the Cys residue, and alkylated in the dark at 37° C. for 30 minutes. After passing the reaction solution at a flow rate of 1 ml/min through the RP-304 (5μ, C4, 300A) column (4.6φ×250 mm) manufactured by Bio-Rad™ previously equilibrated with a 0.1% TFA solution, the column was extensively washed by passing 15 ml of the 0.1% TFA solution at a flow rate of 1 ml/min. Then, by a gradient method in which acetonitrile concentration was increased, the constituent peptides were eluted. The eluate was monitored at A220 nm. It was purified under the following RP-HPLC condition.

RP-HPLC Condition

High performance liquid chromatography instrument: 5000 LC manufactured by Varian™

Column: RP-304 (5μ, C4, 300A) column (4.6φ×250 mm) manufactured by Bio-Rad™

Flow rate: 1 ml/min

Eluent A: 0.1% TFA, eluent B: 0.1% TFA-95% acetonitrile

Gradient elution condition: As described in Table 7

TABLE 7

| Time: min | 0 | 10 | 40 | 60 |
|---|---|---|---|---|
| Solution B % | 0 | 25 | 50 | 100 |

Detection: A220 nm, 0.08–0.16 aufs

3) Analysis of Amino Acid Composition

To 20–100 μl of the fragmented peptide solution of the purified IFN-α subtype IIIe, 1 nmol of Nle was added as an internal standard, which was then concentrated under reduced pressure in a speedvac concentrator. 0.2 ml of constant boiling hydrochloric acid containing 0.1% thioglycolic acid was added, and then sealed and hydrolyzed at 110° C. for 24 hours. Using the automatic amino acid analyzer model 835 manufactured by Hitachi Seisakusho, the constituent amino acids that formed were analyzed by the OPA hypo method, and amino sugars and Trp were analyzed by the OPA method.

4) Sequencing of Amino Terminal-amino Acids

The fragmented peptide solution of the purified IFN-α subtype IIIe were subjected to automatic Edman degradation using the gas-phase type protein sequencer model 477A manufactured by Applied Biosystems™, and the PTH-amino acids that formed were identified using the PTH-amino acid analyzer model 120A manufactured by Applied Biosystems™.

Experimental Results and Discussion

1) Structural Analysis of Cyanogen Bromide-fragmented Peptides

After 30 μg of the IFN-α subtype IIIe was fragmented with cyanogen bromide, the reductive-carboxymethylated peptides were purified with the RP-304 (5μ, C4, 300A) column (4.6φ×250 mm) manufactured by Bio-Rad™. Each peptide was subjected to amino acid analysis, amino sugar analysis, and amino acid sequencing. For peak fractions corresponding to SEQ ID NO: 21–60, SEQ ID NO: 61–106, SEQ ID NO: 113–149, and SEQ ID NO: 150–166, amino acid sequences were identified.

2) Structural Analysis of Trypsin-fragmented Peptides

After 80 μg of the IFN-α subtype IIIe was fragmented with trypsin, the reductive-carboxymethylated peptide was purified with the RP-304 column. Each peptide was subjected to amino acid analysis, amino sugar analysis, and amino acid sequencing. For peak fractions corresponding to SEQ ID NO: 1–12, SEQ ID NO: 14–23, SEQ ID NO: 24–50, SEQ ID NO: 51–84, SEQ ID NO: 85–121, SEQ ID NO: 122–126, SEQ ID NO: 136–145, SEQ ID NO: 146–150 and SEQ ID NO: 151–160, amino acid sequences were identified.

As hereinabove described, the cyanogen bromide-fragmentation and trypsin-fragmentation of the IFN-α subtype IIIe and the following structural analysis of the constituent peptides confirmed that the IFN-α subtype IIIe is comprised of 166 amino acid residues. The identification result of all amino acid sequences is shown in SEQ ID NO: 4. The primary structure of the subtype IIIe was similar to that of the previously published IFN-α10a (=–αC) (Nature Mar. 5, 1981: 290, 20–26), except that the sequence was novel in that the amino acid at position 19 was Ala in stead of Gly.

EXAMPLE 3
Gene Cloning of the IFN-α Subtype IIIe

The gene of the IFN-α subtype IIIe was specifically amplified by PCR. As primers, U-10 (SEQ ID NO: 6) and L-10 (SEQ ID NO: 7), sequences that are specific to the subtype IIIe, were used. Since the IFN-α gene contained no introns, genomic DNA was used as a template for PCR. The experimental method is described below.

The genomic DNA of Namalwa cell was prepared using the DNA Extraction kit (Stratagene™) and was used as the template for PCR. PCR was performed under the following condition using KOD DNA polymerase (Toyobo™), and primers U-10 and L-10. Thus, a reaction mixture comprising 1 μg of the template DNA, 0.5 μg of each primer, 1×KOD buffer, 1 mM $MgCl_2$, 200 μM of each DNTP, and 2.5 U KOD was subjected to, after heating at 90° C. for 3 minutes, 30 cycles of PCR with each cycle comprising 95° C. for 30 seconds, 68° C. for 30 seconds, and 72° C. for 90 seconds, and then cooled at 4° C.

This PCR product was cloned into pUC18 vector to obtain a recombinant plasmid of the IFN-α subtype IIIe.

Thereafter, using the ABI PRISM™ Dye Terminator Cycle Sequencing Ready Reaction Kit (Perkin-Elme™) the above plasmid was subjected to a dye-terminator reaction, and using the ABI PRISM™ 377 DNA Sequencer (Perkin-Elmer™) the base sequence was analyzed. The determined base sequence (567 bp) is shown in SEQ ID NO: 1, and the amino acid sequence (189 amino acids) deduced from said base sequence is shown in SEQ ID NO: 3. The sequence of the amino acid sequence at position 24 and after of SEQ ID NO: 3 completely coincided with the amino acid sequence (SEQ ID NO: 4) determined in the above Example 2. The sequence at positions 1–23 of the amino acid sequence as set forth in SEQ ID NO: 3 corresponds to the signal sequence.

In the comparison of the base sequence of IIIe as set forth in SEQ ID NO: 1 with the previously reported base sequence of IFN-α10a, three bases (positions 66, 96, and 125) were different.

As described above, for the novel IFN-α subtype IIIe, a complete DNA sequence containing the signal sequence portion was obtained.

INDUSTRIAL APPLICABILITY

The present invention can provide a novel human IFN-α and its derivative having an unprecedentedly high specific activity, and a pharmaceutical composition comprising said IFN-α and its derivative as active ingredient.

Sequence Listing Free Text

The amino acids at positions 1, 29, and 37 as set forth in SEQ ID NO: 5 are unknown.

---

What is claimed is:

1. Isolated DNA comprising the base sequence as set forth in SEQ ID NO: 1 or SEQ ID NO: 2, or isolated DNA encoding a protein comprising the amino acid sequence as set forth in SEQ ID NO: 3 or SEQ ID NO: 4.

2. Isolated DNA encoding a protein comprising an amino acid sequence in which 1–5 amino acid residues in the amino acid sequence as set forth in SEQ ID NO: 3 or SEQ ID NO: 4 have been replaced, deleted, and/or added wherein the protein encoded by said DNA has the following characteristics (a) and (b):

(a) having a specific activity higher than $4.0 \times 10^8$ units/mg as measured by an anti-viral activity assay on Sindbis virus using the FL cell, a human-derived cultured cell; and (b) migrating as a band with an apparent molecular weight of 20 kDa–23 kDa by sodium dodecyl sulfate-polyacrylamide gel electrophoresis after reduction treatment.

3. An expression vector having the DNA according to claim 1.

4. A transformant transformed with the expression vector according to claim 3.

5. A method of producing a recombinant human interferon-α or its derivative, which method comprises culturing the transformant according to claim 4 and recovering the expressed recombinant human interferon-α or its derivative.

* * * * *

UNITED STATES PATENT AND TRADEMARK OFFICE
CERTIFICATE OF CORRECTION

PATENT NO. : 6,703,225 B1
DATED : March 9, 2004
INVENTOR(S) : Kojima et al.

It is certified that error appears in the above-identified patent and that said Letters Patent is hereby corrected as shown below:

Title Page,
Item [22], PCT Filed, change "Jan. 4, 2000" to -- Jan. 5, 2000 --.

Signed and Sealed this

Third Day of August, 2004

JON W. DUDAS
*Acting Director of the United States Patent and Trademark Office*

SEQUENCE LISTING

<160> NUMBER OF SEQ ID NOS: 7

<210> SEQ ID NO 1
<211> LENGTH: 567
<212> TYPE: DNA
<213> ORGANISM: Homo sapiens

<400> SEQUENCE: 1

```
atg gcc ctg tcc ttt tct tta ctt atg gcc gtg ctg gtg ctc agc tac      48
Met Ala Leu Ser Phe Ser Leu Leu Met Ala Val Leu Val Leu Ser Tyr
                  5                  10                  15 aaa tcc atc tgt tct cta ggc tgt gat ctg cct cag acc cac agc ctg      96
Lys Ser Ile Cys Ser Leu Gly Cys Asp Leu Pro Gln Thr His Ser Leu
             20                  25                  30 ggt aat agg agg gcc ttg ata ctc ctg gca caa atg gga aga atc tct     144
Gly Asn Arg Arg Ala Leu Ile Leu Leu Ala Gln Met Gly Arg Ile Ser
         35                  40                  45 cct ttc tcc tgc ctg aag gac aga cat gat ttc cga atc ccc cag gag     192
Pro Phe Ser Cys Leu Lys Asp Arg His Asp Phe Arg Ile Pro Gln Glu
     50                  55                  60 gag ttt gat ggc aac cag ttc cag aag gct caa gcc atc tct gtc ctc     240
Glu Phe Asp Gly Asn Gln Phe Gln Lys Ala Gln Ala Ile Ser Val Leu
 65                  70                  75                  80 cat gag atg atc cag cag acc ttc aat ctc ttc agc aca gag gac tca     288
His Glu Met Ile Gln Gln Thr Phe Asn Leu Phe Ser Thr Glu Asp Ser
                 85                  90                  95 tct gct gct tgg gaa cag agc ctc cta gaa aaa ttt tcc act gaa ctt     336
Ser Ala Ala Trp Glu Gln Ser Leu Leu Glu Lys Phe Ser Thr Glu Leu
            100                 105                 110 tac cag caa ctg aat gac ctg gaa gca tgt gtg ata cag gag gtt ggg     384
Tyr Gln Gln Leu Asn Asp Leu Glu Ala Cys Val Ile Gln Glu Val Gly
        115                 120                 125 gtg gaa gag act ccc ctg atg aat gag gac tcc atc ctg gct gtg agg     432
```

```
Val Glu Glu Thr Pro Leu Met Asn Glu Asp Ser Ile Leu Ala Val Arg
        130                 135                 140 aaa tac ttc caa aga atc act ctt tat cta ata gag agg aaa tac agc       480
Lys Tyr Phe Gln Arg Ile Thr Leu Tyr Leu Ile Glu Arg Lys Tyr Ser
145                 150                 155                 160 cct tgt gcc tgg gag gtt gtc aga gca gaa atc atg aga tcc ctc tcg       528
Pro Cys Ala Trp Glu Val Val Arg Ala Glu Ile Met Arg Ser Leu Ser
                165                 170                 175 ttt tca aca aac ttg caa aaa aga tta agg agg aag gat                   567
Phe Ser Thr Asn Leu Gln Lys Arg Leu Arg Arg Lys Asp
                180                 185

<210> SEQ ID NO 2
<211> LENGTH: 498
<212> TYPE: DNA
<213> ORGANISM: Homo sapiens

<400> SEQUENCE: 2 tgt gat ctg cct cag acc cac agc ctg ggt aat agg agg gcc ttg ata        48
Cys Asp Leu Pro Gln Thr His Ser Leu Gly Asn Arg Arg Ala Leu Ile
                5                   10                  15 ctc ctg gca caa atg gga aga atc tct cct ttc tcc tgc ctg aag gac        96
Leu Leu Ala Gln Met Gly Arg Ile Ser Pro Phe Ser Cys Leu Lys Asp
                20                  25                  30 aga cat gat ttc cga atc ccc cag gag gag ttt gat ggc aac cag ttc       144
Arg His Asp Phe Arg Ile Pro Gln Glu Glu Phe Asp Gly Asn Gln Phe
            35                  40                  45 cag aag gct caa gcc atc tct gtc ctc cat gag atg atc cag cag acc       192
Gln Lys Ala Gln Ala Ile Ser Val Leu His Glu Met Ile Gln Gln Thr
        50                  55                  60 ttc aat ctc ttc agc aca gag gac tca tct gct gct tgg gaa cag agc       240
Phe Asn Leu Phe Ser Thr Glu Asp Ser Ser Ala Ala Trp Glu Gln Ser
65                  70                  75                  80 ctc cta gaa aaa ttt tcc act gaa ctt tac cag caa ctg aat gac ctg       288
Leu Leu Glu Lys Phe Ser Thr Glu Leu Tyr Gln Gln Leu Asn Asp Leu
                85                  90                  95 gaa gca tgt gtg ata cag gag gtt ggg gtg gaa gag act ccc ctg atg       336
Glu Ala Cys Val Ile Gln Glu Val Gly Val Glu Glu Thr Pro Leu Met
                100                 105                 110 aat gag gac tcc atc ctg gct gtg agg aaa tac ttc caa aga atc act       384
Asn Glu Asp Ser Ile Leu Ala Val Arg Lys Tyr Phe Gln Arg Ile Thr
            115                 120                 125 ctt tat cta ata gag agg aaa tac agc cct tgt gcc tgg gag gtt gtc       432
Leu Tyr Leu Ile Glu Arg Lys Tyr Ser Pro Cys Ala Trp Glu Val Val
        130                 135                 140 aga gca gaa atc atg aga tcc ctc tcg ttt tca aca aac ttg caa aaa       480
Arg Ala Glu Ile Met Arg Ser Leu Ser Phe Ser Thr Asn Leu Gln Lys
145                 150                 155                 160 aga tta agg agg aag gat                                               498
Arg Leu Arg Arg Lys Asp
                165

<210> SEQ ID NO 3
<211> LENGTH: 189
<212> TYPE: PRT
<213> ORGANISM: Homo sapiens

<400> SEQUENCE: 3

Met Ala Leu Ser Phe Ser Leu Leu Met Ala Val Leu Val Leu Ser Tyr
                5                   10                  15

Lys Ser Ile Cys Ser Leu Gly Cys Asp Leu Pro Gln Thr His Ser Leu
```

```
                20                  25                  30
Gly Asn Arg Arg Ala Leu Ile Leu Ala Gln Met Gly Arg Ile Ser
            35                  40                  45

Pro Phe Ser Cys Leu Lys Asp Arg His Asp Phe Arg Ile Pro Gln Glu
        50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
130                 135                 140

Lys Tyr Phe Gln Arg Ile Thr Leu Tyr Leu Ile Glu Arg Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185

<210> SEQ ID NO 4
<211> LENGTH: 166
<212> TYPE: PRT
<213> ORGANISM: Homo sapiens

<400> SEQUENCE: 4

Cys Asp Leu Pro Gln Thr His Ser Leu Gly Asn Arg Arg Ala Leu Ile
                5                   10                  15

Leu Leu Ala Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 5
<211> LENGTH: 40
<212> TYPE: PRT
<213> ORGANISM: Homo sapiens
<220> FEATURE:
```

```
<221> NAME/KEY: MOD_RES
<222> LOCATION: (1)
<223> OTHER INFORMATION: Unknown amino acid
<221> NAME/KEY: MOD_RES
<222> LOCATION: (29)
<223> OTHER INFORMATION: Unknown amino acid
<221> NAME/KEY: MOD_RES
<222> LOCATION: (37)
<223> OTHER INFORMATION: Unknown amino acid

<400> SEQUENCE: 5

Xaa Asp Leu Pro Gln Thr His Ser Leu Gly Asn Arg Arg Ala Leu Ile
                  5                  10                  15

Leu Leu Ala Gln Met Gly Arg Ile Ser Pro Phe Ser Xaa Leu Lys Asp
             20                  25                  30

Arg His Asp Phe Xaa Ile Pro Gln
         35                  40

<210> SEQ ID NO 6
<211> LENGTH: 30
<212> TYPE: DNA
<213> ORGANISM: Homo sapiens

<400> SEQUENCE: 6
ataggatcca ggccgaagtt caaggttatc                                            30

<210> SEQ ID NO 7
<211> LENGTH: 34
<212> TYPE: DNA
<213> ORGANISM: Homo sapiens

<400> SEQUENCE: 7
tacaagcttc aggatcattg ccatgttgaa ccag                                       34
```